US010634659B2

(12) United States Patent
Bishop et al.

(10) Patent No.: US 10,634,659 B2
(45) Date of Patent: Apr. 28, 2020

(54) TEST STRIP EJECTOR FOR MEDICAL DEVICE

(71) Applicant: Roche Diabetes Care, Inc., Indianapolis, IN (US)

(72) Inventors: Will A. Bishop, Noblesville, IN (US); James R. Hanson, Brownsburg, IN (US); Joyce A. Trese, Cicero, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 29 days.

(21) Appl. No.: 16/008,408

(22) Filed: Jun. 14, 2018

(65) Prior Publication Data

US 2018/0292379 A1    Oct. 11, 2018

Related U.S. Application Data

(62) Division of application No. 15/296,367, filed on Oct. 18, 2016, now Pat. No. 10,048,247, which is a division of application No. 13/761,465, filed on Feb. 7, 2013, now Pat. No. 9,494,569.

(51) Int. Cl.
*G01N 33/487* (2006.01)
*G01N 27/327* (2006.01)
*G01N 35/00* (2006.01)

(52) U.S. Cl.
CPC ..... *G01N 33/4875* (2013.01); *G01N 27/3273* (2013.01); *A61B 2562/0295* (2013.01); *G01N 2035/00108* (2013.01); *G01N 2035/00138* (2013.01); *Y10T 403/591* (2015.01)

(58) Field of Classification Search
CPC .......... G01N 33/4875; G01N 27/3273; G01N 2035/00108; G01N 2035/00138; Y10T 403/591; A61B 2562/0295
See application file for complete search history.

(56) References Cited

U.S. PATENT DOCUMENTS

| 6,189,370 B1 | 2/2001 | Neel et al. |
| 7,585,464 B2 | 9/2009 | Amano et al. |
| 7,819,283 B2 | 10/2010 | Chambers et al. |
| 8,057,753 B2 | 11/2011 | DeAngeli et al. |

(Continued)

FOREIGN PATENT DOCUMENTS

| EP | 1 321 769 A1 | 6/2003 |
| EP | 1 382 968 A1 | 1/2004 |

(Continued)

*Primary Examiner* — Benjamin R Whatley
(74) *Attorney, Agent, or Firm* — Woodard, Emhardt, Henry, Reeves & Wagner, LLP

(57) ABSTRACT

A system for receiving and ejecting a fluid testing device test strip includes a strip connector having first and second guide rails, and divider walls each having a channel. A sled has first and second legs connected to a cross member. Each leg has a contact leg extending inwardly from a chamfered end. The first and second legs when positioned parallel to the guide rails have the contact leg captured in the divider wall channels retaining the sled in sliding contact with the guide rails for motions in loading and ejection directions. A mechanism assembly is movably connected to the fluid testing device. The cross member is coupled so operation in a first direction displaces the sled in the loading direction positioning the sled in a test strip test position, and opposite operation positions the contact legs in direct contact with and ejects the test strip.

10 Claims, 9 Drawing Sheets

(56) References Cited

U.S. PATENT DOCUMENTS

| | | |
|---|---|---|
| 2005/0224345 A1 | 10/2005 | Taniike et al. |
| 2006/0133956 A1 | 6/2006 | Hamanaka |
| 2007/0170200 A1 | 7/2007 | Chambers et al. |
| 2007/0255114 A1 | 11/2007 | Ackermann |
| 2008/0019870 A1 | 1/2008 | Newman et al. |
| 2008/0229808 A1 | 9/2008 | Lee |
| 2009/0108013 A1 | 4/2009 | Van Der Velde et al. |
| 2009/0270765 A1 | 10/2009 | Ghesquiere et al. |
| 2010/0012530 A1 | 1/2010 | Watanbe et al. |
| 2010/0319170 A1 | 12/2010 | Hsu et al. |
| 2011/0008880 A1 | 1/2011 | Uehata et al. |
| 2011/0040160 A1 | 2/2011 | Sakata et al. |
| 2011/0143562 A1 | 6/2011 | Wu et al. |
| 2011/0186588 A1 | 8/2011 | DeAngeli et al. |
| 2011/0189062 A1 | 8/2011 | DeAngeli et al. |
| 2012/0143085 A1 | 6/2012 | Sauers et al. |
| 2014/0005507 A1 | 1/2014 | Hanson et al. |

FOREIGN PATENT DOCUMENTS

| | | |
|---|---|---|
| EP | 1 480 037 A1 | 11/2004 |
| EP | 1 762 848 B1 | 3/2007 |
| EP | 1 983 339 A1 | 10/2008 |
| EP | 2 071 326 A1 | 6/2009 |
| EP | 2 264 450 A2 | 12/2010 |
| JP | 2003-114213 A | 4/2003 |
| JP | 2004-101514 A | 4/2004 |
| WO | WO 2002/08753 A2 | 1/2002 |
| WO | WO 2004/063747 A1 | 7/2004 |
| WO | WO 2005/080966 A1 | 9/2005 |
| WO | WO 2007/083773 A1 | 7/2007 |
| WO | WO 2008/016137 A1 | 2/2008 |
| WO | WO 2009/055643 A2 | 4/2009 |
| WO | WO 2011/095775 A1 | 8/2011 |

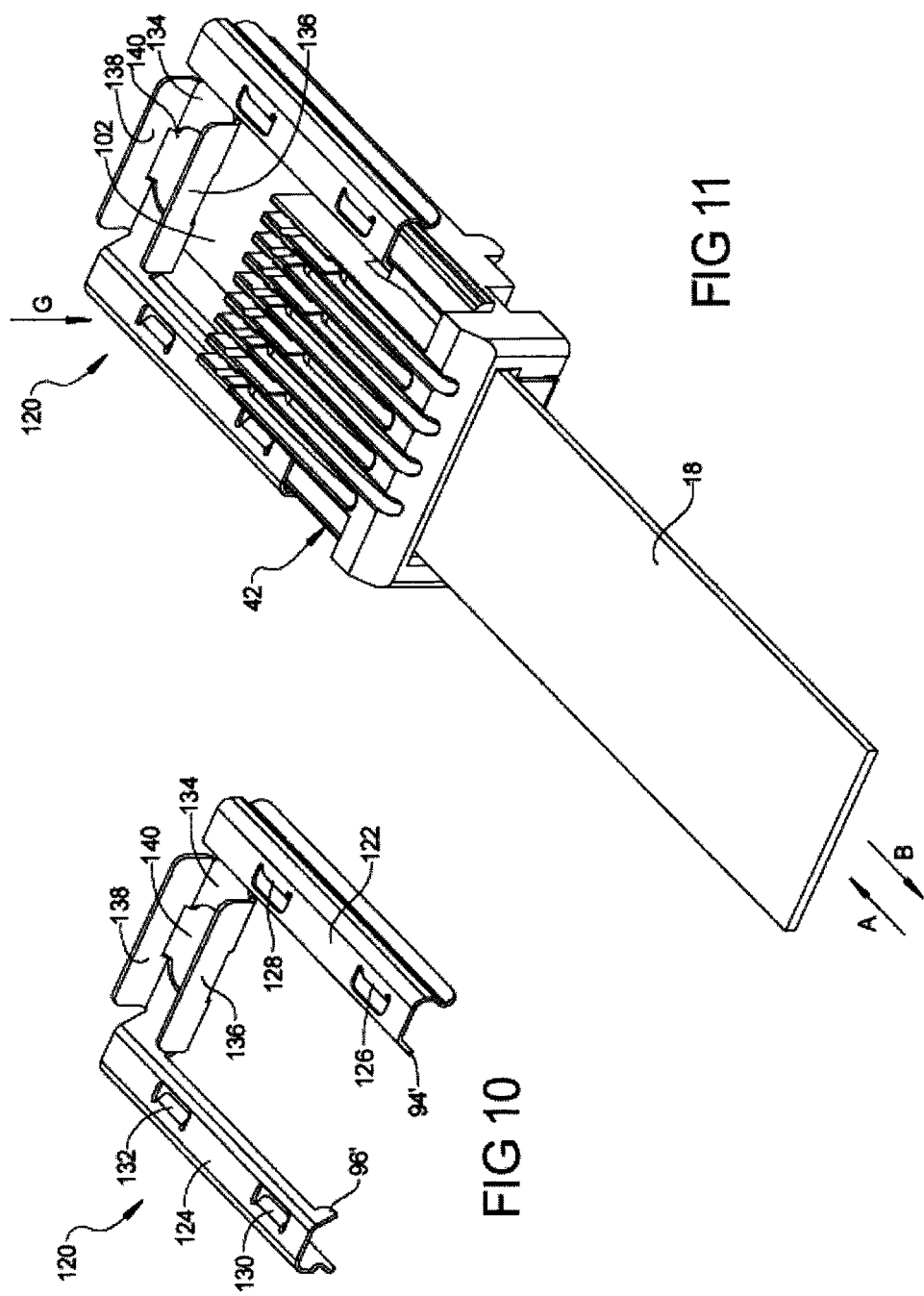

TEST STRIP EJECTOR FOR MEDICAL DEVICE

CROSS REFERENCE TO RELATED APPLICATIONS

This application is a divisional of U.S. patent application Ser. No. 15/296,367 filed Oct. 18, 2016, now U.S. Pat. No. 9,494,569, which is a divisional of U.S. patent application Ser. No. 13/761,465 filed Feb. 7, 2013, which are hereby incorporated by reference.

FIELD

The present disclosure relates to a device and method for loading and then ejecting a sample containing test strip following measurement.

BACKGROUND

Medical devices are often used as diagnostic devices and/or therapeutic devices in diagnosing and/or treating medical conditions of patients. For example, a blood glucose meter is used as a diagnostic device to measure blood glucose levels of patients suffering from diabetes. Blood glucose meters use a test strip that receives a blood sample of the patient. The test strip has electrical contacts on the strip that are electrically contacted when the test strip is inserted into the meter. The meter determines a blood glucose level by measuring currents passed through the electrical contacts of the strip, and provides for readout of the glucose level.

Known meters receive the test strip in an insertion direction that also engages the electrical strip conductors of the test strip with the electrical contacts of the meter. As the test strip is loaded by the user, the insertion motion is used to drive the electrical contacts of the test strip into engagement with the contacts of the meter. The strip ejection system permits ejection of the dosed test strip following testing without further contact of the test strip by the user. Any interference with or sliding contact of the electrical contacts of the test strip during insertion, however, can damage the electrical contacts or misalign one or more of the contacts. A force applied to eject the test strip of known strip ejection systems can also cause racking or rotation of the test strip which can bind the test strip or interfere with ejection.

For example, the measurement device of U.S. Published Patent Application No. 2010/0012530 to Watanabe et al. includes a pushing member having projection part that is slidably guided within a pushing member cover. Clearance between the projection part and pushing member therefore limits the control available to reduce deflection of pushing member during its travel to displace a sensor. In addition, pushing member includes a single substantially centrally positioned projection part guided in a notch. Control of racking of the pushing member during travel is limited by the tolerances between the projection part and pushing member cover, and between the projection part and notch. A braking system having a first braking part in contact with a side wall of the sensor is provided to slow down the exit speed of the sensor. This system does not preclude racking of either the pushing member or the sensor, has only the single projection part to contact and drive the sensor which can therefore be off-center of the sensor, and adds the complexity of a braking system to limit ejection velocity.

European Patent Application EP 1321769 to Pugh appears to disclose a test strip dispensing system having strip push members guided between rails. Rails of this design are positioned external to the strip push members. The strip push members include outer wall areas such as ledges acting as guides. The ledges, however, are positioned within the rails; therefore, continuous positive contact between the strip push members, and the rails to limit racking is not provided and racking can occur due to a tolerance between the components. The design of strip push members and rails also precludes installation in a direction perpendicular to the push member travel direction.

European Patent Application EP 1321769 to Pugh appears to disclose a test strip dispensing system having strip push members 116, 210 guided between rails 100 or 214. Rails of this design are positioned external to the strip push members. The strip push members include outer wall areas such as ledges 220 acting as guides. Ledges 220, however, are positioned within the rails 214; therefore, continuous positive contact between the strip push members 116, 210 and the rails to limit racking is not provided and racking can occur due to a tolerance between the components. The design of strip push members 116, 210 and rails 100, 214 also precludes installation in a direction perpendicular to the push member travel direction.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

In one embodiment of the disclosure, a test strip ejector system for receiving and ejecting a test strip of a fluid testing device includes a strip connector including first and second guide rails, and first and second divider walls between the first and second guide rails, each of the first and second divider walls having a channel. A sled has parallel first and second legs connected to a cross member. Each of the legs has a contact leg extending inwardly from a chamfered end. The first and second legs when positioned in an orientation parallel to the first and second guide rails has the contact leg of each of the first and second legs captured in the channel of one of the first or second divider walls acting to retain the sled in sliding continuous contact with the first and second guide rails for sled motion in each of a loading direction and an ejection direction. A mechanism assembly is movably connected to the fluid testing device. The cross member of the sled is coupled to the mechanism assembly such that operation of the mechanism assembly in a first direction displaces the sled in the loading direction to position the sled in a test strip test position, and opposite operation of the mechanism assembly in a second direction displaces the sled in the ejection direction away from the test strip test position and to position the contact legs in direct contact with the test strip to eject the test strip from the fluid testing device by sled travel toward a test strip ejection position.

In another embodiment, a test strip ejector system for receiving and ejecting a test strip of a fluid testing device includes a strip connector including first and second guide rails, and first and second divider walls positioned between the first and second guide rails. Each of the first and second divider walls has a channel. A sled has parallel first and second legs connected to a cross member. The cross member is received in a cavity between the first and second guide rails. Each of the legs has a contact leg extending inwardly from a free end. The first and second legs when positioned in an orientation parallel to the first and second guide rails have the contact leg of each of the first and second legs captured in the channel of one of the first or second divider walls thereafter retaining the sled in sliding continuous contact with the first and second guide rails for sled motion in each of a loading direction and an ejection direction. A mechanism assembly is movably connected to the fluid testing device. The cross member of the sled is coupled to the mechanism assembly such that operation of the mechanism assembly in a first direction displaces the sled in the loading direction to position the sled in a test strip test position, and opposite operation of the mechanism assembly in a second direction displaces the sled in the ejection direction away from the test strip test position and to position the contact legs in direct contact with the test strip to eject the test strip from the fluid testing device by sled travel toward a test strip ejection position. According to further aspects, a biasing member connected to the mechanism assembly acts to bias the mechanism assembly in the first direction automatically returning the sled to the test strip test position after displacement to the test strip ejection position.

In a further embodiment, a method is provided for receiving and ejecting a test strip by a mechanism assembly of a fluid testing device. The mechanism assembly includes a strip connector including first and second guide rails and first and second divider walls positioned between the first and second guide rails. Each of the first and second divider walls has a channel. A sled has parallel first and second legs connected to a cross member separating the first and second legs by an initial spacing. Each of the legs has a chamfered end and a contact leg extending inwardly from the chamfered end. The legs initially displace outwardly with respect to the initial spacing with the chamfered end positioned parallel with respect to the guide rails such that the contact leg of each of the first and second legs is received in the channel of one of the first or second divider walls. The first and second legs subsequently when rotated to an orientation parallel to the first and second guide rails allow the legs to spring back to the initial spacing thereby capturing the contact leg of each of the first and second legs in the channel to retain the sled in sliding continuous contact with the first and second guide rails for sled motion in each of a loading direction and an ejection direction. A member is movably connected to the fluid testing device. The cross member of the sled is coupled to the member such that member movement in a first direction displaces the sled in the loading direction to position the sled in a test strip test position, and opposite member movement in a second direction operates to displace the sled in the ejection direction away from the test strip test position and to position the contact legs in direct contact with the test strip to eject the test strip from the fluid testing device by sled travel toward a test strip ejection position.

In a further embodiment of the disclosure, the system includes parallel first and second guide rails defining a rail cavity between the guide rails. A sled has opposed first and second legs each positively and continuously slidably engaged to one of the first or second guide rails thereby limiting the sled to only sliding motion in either a loading direction or an opposite ejection direction. The first and second legs are connected by a cross member at one end of the legs. The sled has first and second contact legs in direct contact with the test strip between the guide rails during sliding motion in at least the ejection direction. An actuator arm is rotatably connected to a manually operated mechanism assembly. An engagement post of the actuator arm is received and retained in an elongated slot of the cross member such that sliding motion of the sled in the loading direction and rotation of the actuator arm positions the sled in a test strip test position, and opposite rotation of the actuator arm operates to displace the sled in the ejection direction and to eject the test strip.

In further embodiments, a fluid testing medical device adapted for testing and rejection of a test strip includes a strip connector positioned in the device. A test strip when positioned in a test position makes electrical contact with the strip connector. A test strip ejector system is connected to the device which includes: first and second guide rails; a sled having opposed first and second legs connected at one end by a cross member, each of the legs externally slidably connected to one of the first or second guide rails for sled motion in each of a loading direction and an ejection direction; and a mounting pin connected to the printed circuit board. A button body has an elongated slot receiving the mounting pin allowing the button body to slide inwardly and outwardly with respect to the fluid testing medical device. An actuator arm is rotatably coupled to the mounting pin and is rotatably connected to each of the button body and the cross member of the sled such that inward sliding motion of the button body induces axial rotation of the actuator arm and displacement of the sled in the ejection direction.

In further embodiments, the test meter includes a glucose test meter having a test strip ejector system for receiving and ejecting a test strip. The test meter includes a meter body having a printed circuit board positioned therein. Parallel first and second guide rails of a strip connector are connected to the printed circuit board, the first and second guide rails defining a cavity between the guide rails. A sled has first and second legs each having a contact leg extending into the cavity. The first and second legs are connected by a cross member. Each of the legs is connected externally to and is slidably coupled with respect to one of the first or second guide rails thereby limiting displacement of the sled to only sliding motion in either a loading direction or an opposite ejection direction. A test strip when disposed in the cavity directly contacts the contact legs during motion in at least the ejection direction motion. An actuator arm is rotatably connected to a mechanism assembly. The actuator arm has an engagement post contacting the cross member such that sliding motion of the sled in the loading direction and rotation of the actuator arm positions the sled in a test strip test position, and opposite rotation of the actuator arm operates to displace the sled in the ejection direction and to eject the test strip.

In further embodiments, methods for receiving and ejecting a test strip of a fluid testing device are provided.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

BRIEF DESCRIPTION OF THE DRAWINGS

FIG. 10 shows a top left perspective view of another aspect of a sled of the present disclosure; and FIG. 11 shows a top left perspective view of the sled of FIG. 10 assembled with the strip connector during receipt of a test strip.

Figure 1:
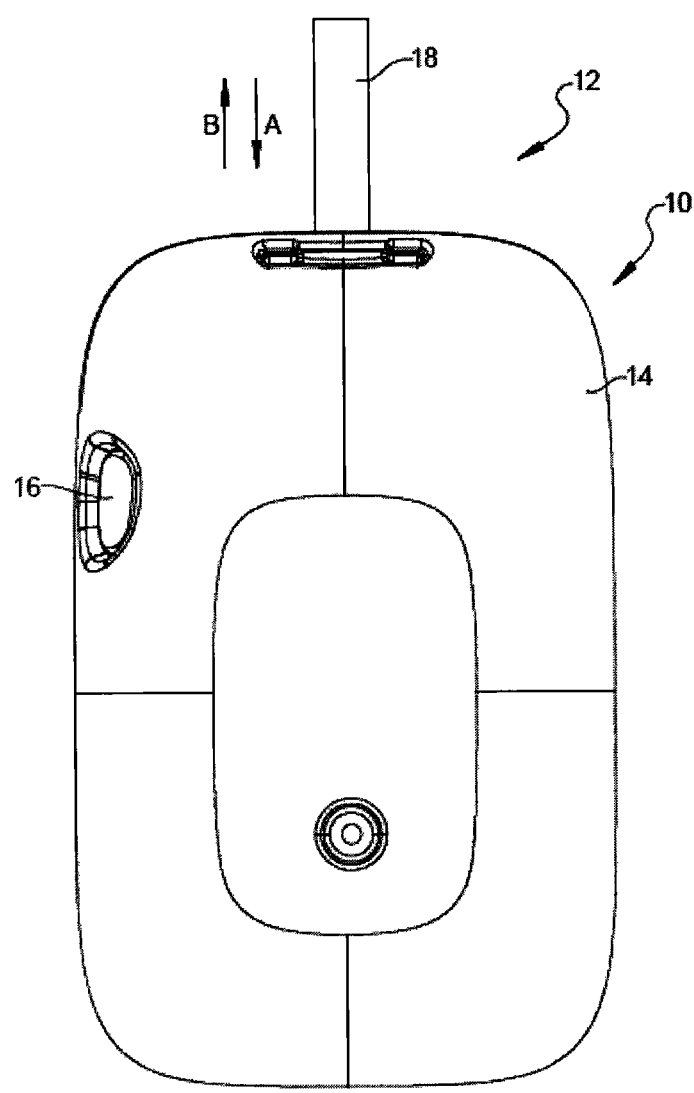
FIG. 1 shows a rear plan view of a fluid analysis device having a test strip ejector of the present disclosure.

Corresponding reference numerals indicate corresponding parts throughout the several views of the drawings. The drawings described herein are for illustrative purposes only of selected embodiments and not all possible implementations, and are not intended to limit the scope of the present disclosure.

DETAILED DESCRIPTION

Example embodiments will now be described more fully with reference to the accompanying drawings.

Referring now to FIG. 1, an analysis device 10 of a test strip ejector system 12, which can be used for example for testing blood glucose levels, includes a housing 14 upon which a digital readout is provided indicating the results of a body fluid test conducted by the analysis device 10. An ejection button 16 is depressed following completion of the test to eject a test strip 18 which was previously received in a loading direction "A" in housing 14. Upon depression of the ejection button 16, the test strip 18 is ejected in an ejection direction "B". The user of the test strip 18 initially inserts test strip 18 into analysis device 10 so the test strip 18 is recognized, and then removes and doses and then again manually inserts the dosed test strip 18 in the loading direction "A". After analyses, subsequent operation of ejection button 16 ejects the test strip 18. Alternately, the user can manually pull the test strip 18 in the ejection direction "B" to manually remove the test strip.

Figure 2:
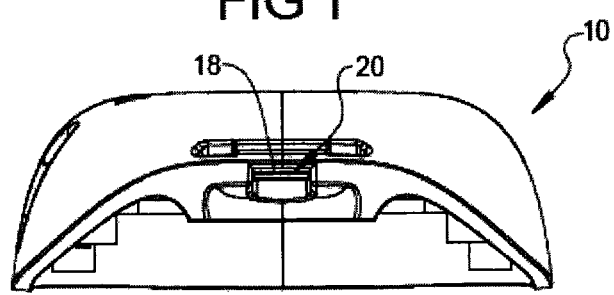
FIG. 2 shows a front elevational end view of the analysis device of FIG. 1.

Referring to FIG. 2, test strip 18 is slidably received via a test strip receiving passage 20 created in a first end of analysis device 10. The test strip receiving passage 20 is sized to slidably receive the test strip 18 while generally preventing twisting or rotation, such as a racking rotation, due to lateral or side-to-side displacement of the test strip.

Referring to FIG. 3 and again to FIGS. 1 and 2, with the housing 14 removed for clarity, the components of a circuit board assembly 22 are visible. Circuit board assembly 22 includes a printed circuit board (PCB) 24 such as a printed circuit board having multiple components attached thereto. Housing 14 further includes a mechanism assembly 26 which can be biased prior to or upon receipt of the test strip 18 and can apply a displacement force or a biasing force to eject the test strip 18. Mechanism assembly 26 includes ejection button 16 having an integrally connected button body 28 which together are horizontally displaced while being motion limited by an axially elongated mounting pin 30. Mounting pin 30 is extended from a lower housing component through a hole created in PCB 24, or affixed to PCB 24, and has a longitudinal axis 31 oriented perpendicular to the PCB 24. A linking member defining an actuator arm 32 is rotatably connected to mounting pin 30 and rotates when button body 28 and ejection button 16 are horizontally displaced in a button inward displacement direction "C". According to further aspects, mounting pin 30 oriented coaxial to longitudinal axis 31 is an integrally connected portion of actuator arm 32 and extends through PCB 24 into a hole or receiving aperture created in the lower housing component.

The ejection button 16 may be biased using an ejection button biasing member 33 (not completely visible in this view) to return in a return direction "D" to the button extended position shown following depression by the user. Manual depression of ejection button 16 in the button inward displacement direction "C" inwardly horizontally displaces button body 28 inducing actuator arm 32 to rotate with respect to axis 31. Actuator arm 32 is directly connected to a sled 34 by an engagement post 36 integrally extending from actuator arm 32. Rotational motion of actuator arm 32 induces a sliding displacement of sled 34 in the ejection direction "B". The sled 34 is slidably and connectably engaged with respect to opposed and parallel oriented first and second guide rails 38, 40. The first and second guide rails 38, 40 are integral components of a strip connector 42, which is fixedly connected to printed circuit board 24. The sled 34 slides with respect to and is externally engaged to each of the first and second guide rails 38, 40, as will be better described in reference to FIGS. 6 and 7.

Figure 3:
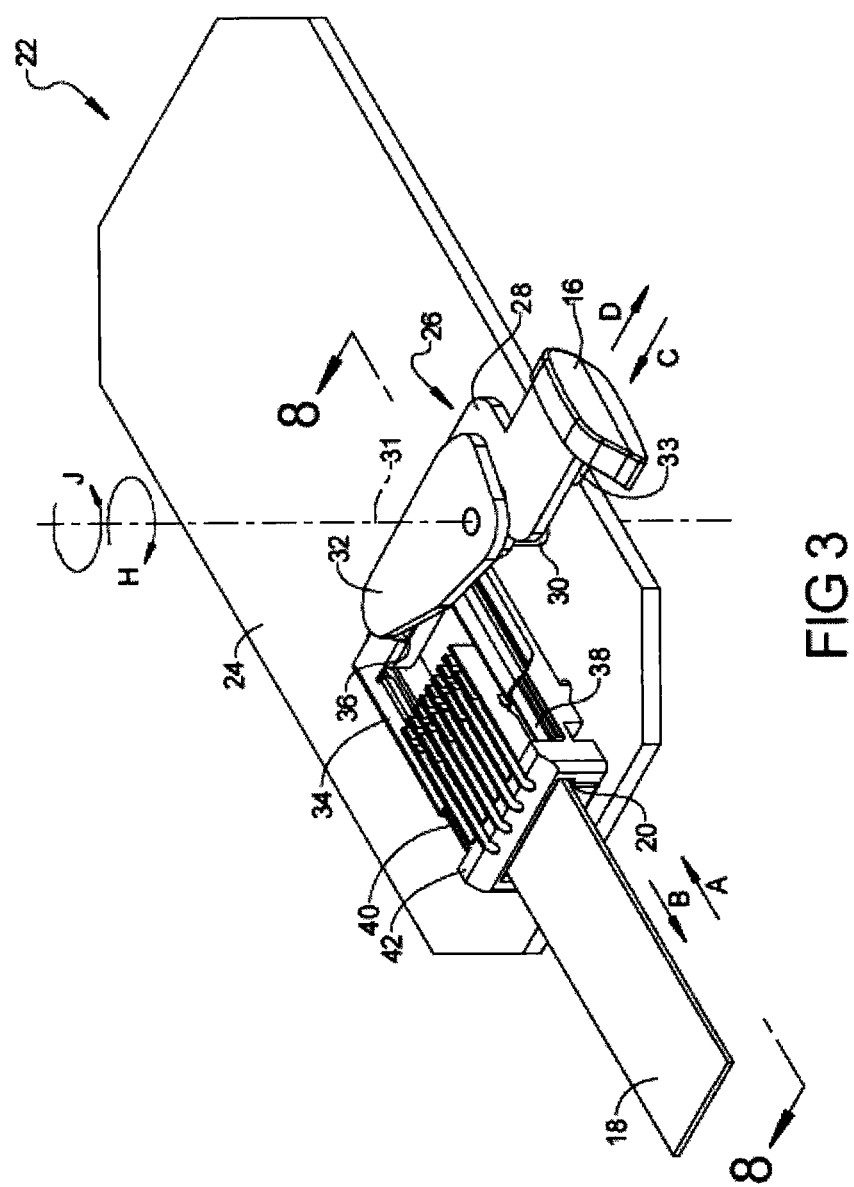
FIG. 3 shows a top left perspective view of a circuit board assembly and test strip ejector of the analysis device of FIG. 1.

Referring to FIG. 4 and again to FIGS. 1-3, the components of mechanism assembly 26 are shown in exploded view for better recognition. The mounting pin 30 includes a first pin portion 44 which is integrally connected to a second pin portion 46. Second pin portion 46 has a smaller diameter than first pin portion 44, thereby creating a pin shoulder 48 which is elevated with respect to PCB 24. The diameter of second pin portion 46 is sized such that second pin portion 46 is slidably received in an elongated slot 50 created in button body 28 when a lower or first surface 52 of button body 28 is supported by and in direct contact with pin shoulder 48. A through aperture 54 also created in button body 28 rotatably receives an arm connecting post 56 which is integrally connected to actuator arm 32 and extends from a first face 58 of actuator arm 32. Arm connecting post 56 is received in through aperture 54 when first face 58 is in direct contact with is supported on a second surface 60 of button body 28. The second pin portion 46 of mounting pin 30 after extending through elongated slot 50 is rotatably received in a pin receiving aperture 62 created in actuator arm 32.

Button body 28 and ejection button 16 are together permitted to slide horizontally in each of the inward displacement direction "C" and the opposite return direction "D" because of the length of elongated slot 50 which receives and thereby directs second pin portion 46. The actuator arm 32, however, which is rotatably mounted to second pin portion 46, is limited to rotation with respect to axis 31. As ejection button 16 and button body 28 are displaced in the inward displacement direction "C" by the user of analysis device 10, the horizontal motion of button body 28 is converted to a rotation of actuator arm 32 as a rotational force acts through arm connecting post 56. It is noted the engagement pin 36 of actuator arm 32 also extends from first face 58. The engagement pin 36 is received in a sled elongated slot 64 created in sled 34. Rotation of actuator arm 32 with respect to pin receiving aperture 62 acts through engagement pin 36 to induce a sliding motion of sled 34 in the ejection direction "B", which directly contacts and therefore ejects test strip 18.

After completion of the test by the analysis device 10, the test strip 18 is ejected from housing 14 by depression of ejection button 16 in the inward displacement direction "C". Actuator arm 32 rotates with respect to axis 31 in a counterclockwise direction as viewed in FIG. 3, having engagement post 36 engaged with sled 34 within sled elongated slot 64, which displaces sled 34 in the ejection direction "B" and thereby discharges test strip 18. The amount of force applied by the user to ejection button 16 directly determines the force applied by actuator arm 32 and engagement post 36 to sled 34 to eject test strip 18. The higher the applied force, the greater the velocity of ejection of test strip 18. Therefore, the force received (Fr) to eject the test strip 18 is a function of the force applied (Fa) to ejection button 16 which is greater than the opposing biasing force (Fo) of ejection button biasing member 33 (Fr=Fa−Fo). Test strip 18 can therefore be ejected with enough force/velocity to direct test strip 18 into a trash or biohazard container (not shown) when not positioned directly over the container, or if analysis device 10 is held directly over the trash or biohazard container, a reduced force applied to ejection button 16 will push test strip 18 out to subsequently fall by gravity. When ejection button 16 is released, the biasing force of ejection button biasing member 33 returns ejection button 16 to its fully extended position.

Figure 4:
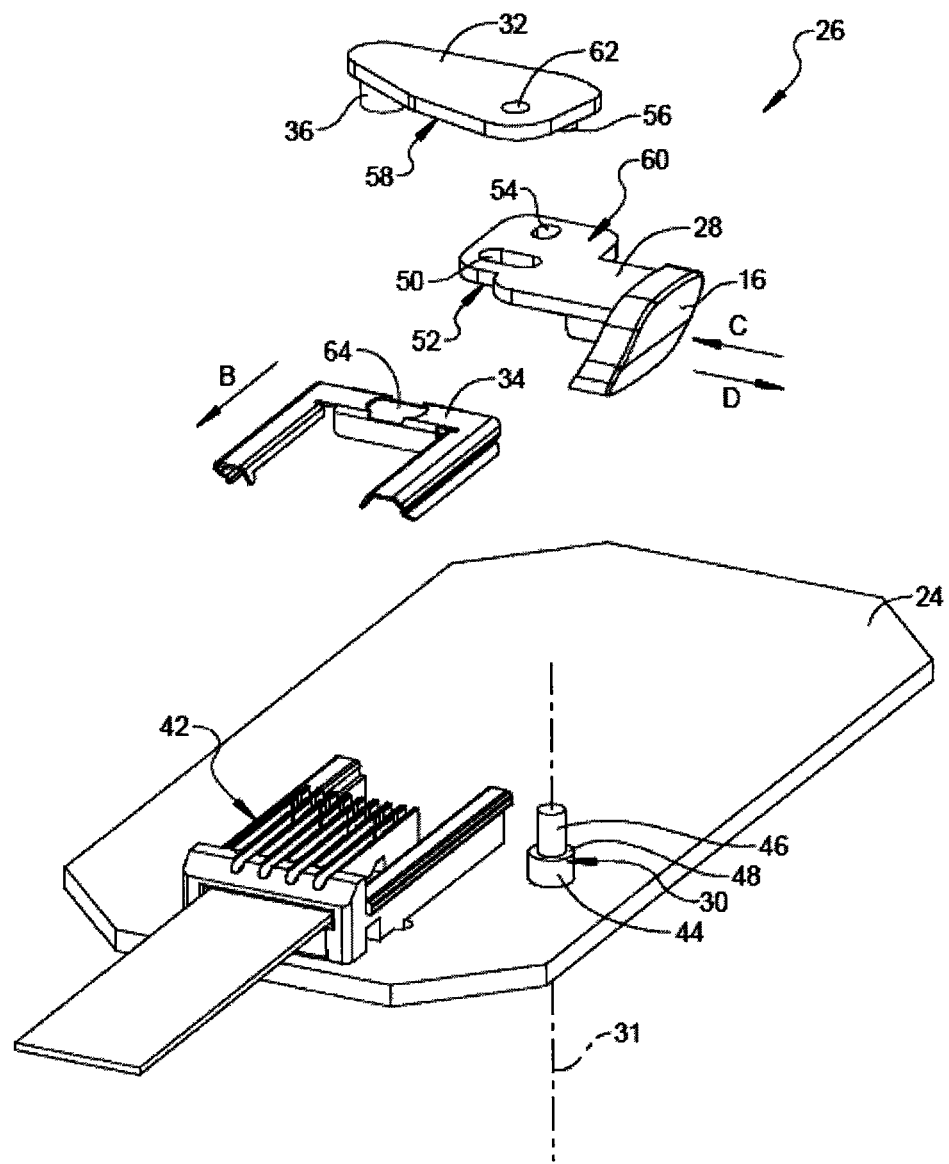
FIG. 4 shows a top left perspective assembly view of the circuit board assembly and test strip ejector similar to FIG. 3.

With continuing reference to FIGS. 3 and 4, the test strip analysis position shown in FIG. 3 can be reached by displacing sled 34 in the loading direction "A" by manual insertion of the test strip 18. The force of insertion of test strip 18 slidably displaces sled 34 in the loading direction "A" which directly rotates the actuator arm 32 in a clockwise direction. As the test strip 18 is inserted in the loading direction "A", direct contact between test strip 18 and sled 34 occurs between the first and second guide rails 38, 40. The elongated slot 50 permits actuator arm 32 to rotate with respect to mounting pin 30 in response to a load applied from a sliding motion in the loading direction "A" of both the test strip 18 and sled 34. In this aspect, the sliding motion of sled 34 is translated into a rotational motion of actuator arm 32 by contact between engagement post 36 and a wall defined by elongated slot 64.

As noted above, displacement of ejection button 16 causes rotation of the button body 28 in a counterclockwise direction as viewed with respect to FIG. 3. As the actuator arm 32 rotates in the counterclockwise direction, a force is applied via contact between actuator arm 32 and engagement post 36 such that the rotational motion of actuator arm 32 is translated into an axial sliding motion of test strip 18 in the ejection direction "B". The test strip 18 which is in direct contact with sled 34 is ejected in the ejection direction "B" as the sled 34 is induced to slide in the ejection direction "B". The test strip 18, during test strip loading in the second aspect described above, and during the ejection step, is in direct contact with each of opposed first and second contact legs 94, 96 which are substantially rigid, integrally connected to sled 34, and positioned between the first and second guide rails 38, 40 which will be described in reference to FIGS. 5-7.

Figure 5:
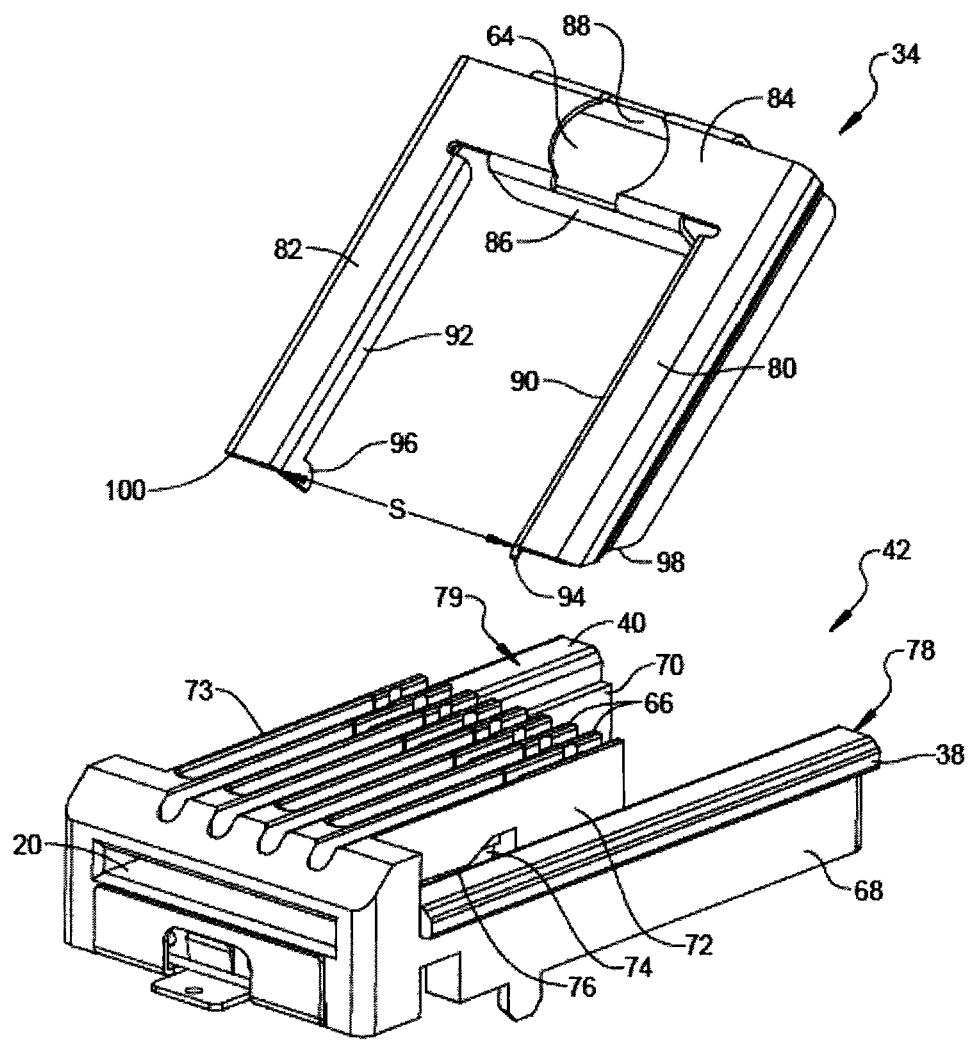
FIG. 5 shows a front perspective view of the sled and strip connector of FIG. 3 prior to installation of the sled.
Figure 9:
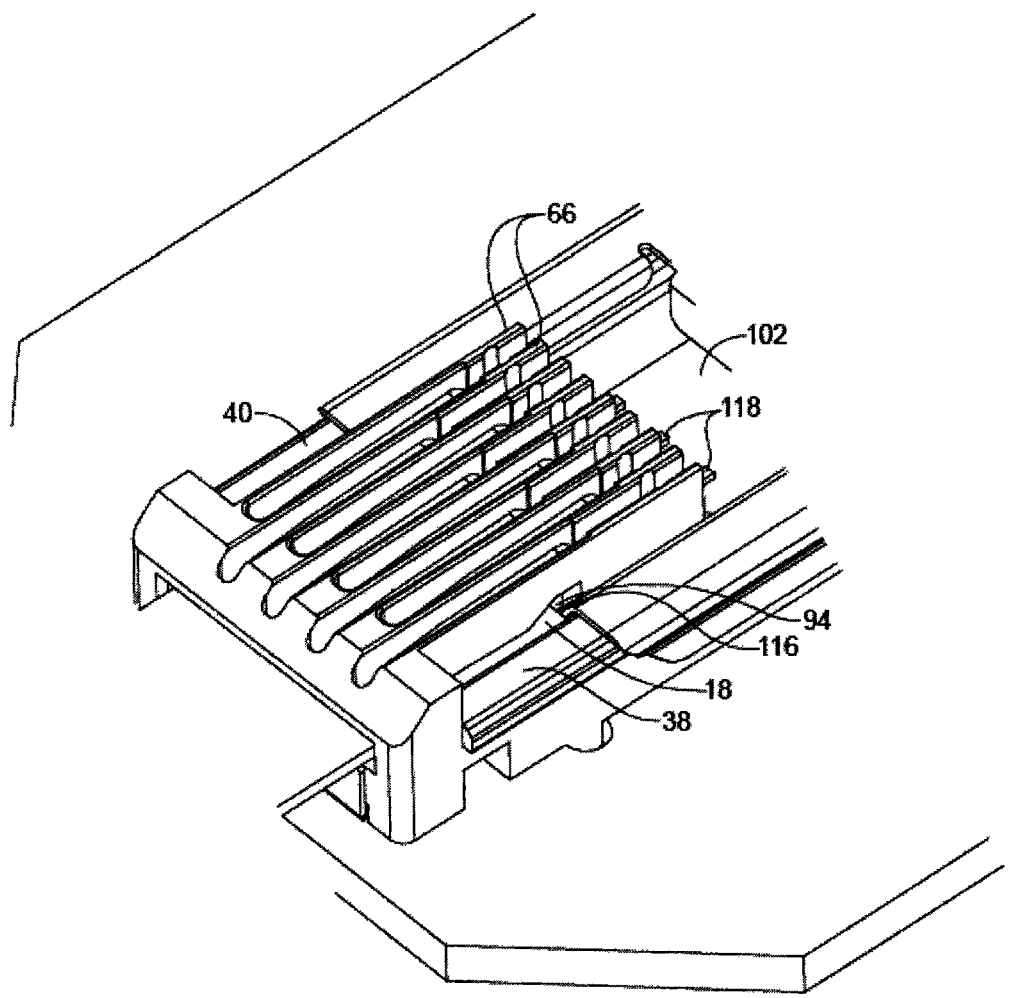
FIG. 9 shows a top left perspective view of the test strip, sled and strip connector showing direct contact between the sled and the test strip.

Referring to FIG. 5, the first and second guide rails 38, 40 are oppositely positioned in a mirror image configuration of each other and have common individual features. Multiple insulator members 66 similar to polymeric material fingers are positioned between first and second guide rails 38, 40, and provide for individual separation of test strip contact members (more clearly visible in FIG. 9). First and second guide rails 38, 40 are substantially rigid and are supported by first and second support walls 68, 70. Opposed and parallel first and second divider walls 72, 73 define boundaries of the insulator members 66. Each of the first and second divider walls 72, 73 includes a wall notch 74 (only a first one of the wall notches is visible in this view). A channel 76 (only one channel 76 is visible in this view) is created between each of the first and second divider walls 72, 73 and its associated first or second support wall 68, 70. Each of the first and second guide rails 38, 40 also includes a smooth, planar surface 78, 79 oriented perpendicular to the first or second support wall 68, 70.

With continuing reference to FIG. 5 and again to FIG. 4, sled 34 further includes opposed and parallel first and second legs 80, 82 which are substantially mirror images of each other. A Cross member 84 is integrally connected between and therefore joins the first and second legs 80, 82. The cross member 84 includes opposed first and second flanges 86, 88 which stiffen the cross member 84 and also provide contact points for the engagement post 36 of the actuator arm 32. The first and second flanges 86, 88 are oppositely positioned about the sled elongated slot 64. Opposed first and second inner ribs 90, 92 are also provided which stiffen and extend for substantially an entire length of each of the first and second legs 80, 82. First inner rib 90 integrally extends from first leg 80 and second inner rib 92 integrally extends from second leg 82. A first contact leg 94 integrally extends inwardly from first inner rib 90 and a second contact leg 96 integrally extends inwardly from second inner rib 92. Each of the first and second legs 80, 82 also includes free end defining a chamfered end 98, 100 (only first chamfered end 98 is clearly visible in this view) whose purpose will be discussed in reference to FIG. 6. The first and second legs 80, 82 are separated by a spacing "S" between the first and second contact legs 94, 96 which are located at free ends of the first and second legs 80, 82. The first and second legs 80, 82 can be elastically displaced apart from each other during installation into the strip connector 42; therefore, the spacing "S" in the nominal position shown will temporarily increase during installation of the sled 34 to allow receipt of the first and second contact legs 94, 96 into the wall notches 74.

According to several embodiments, sled 34 is made of a metal such as stainless steel, to maximize a stiffness-to-weight ratio of sled 34. Other materials for sled 34 can also be used, including plastics. According to several aspects engagement post 36 and actuator arm 32, as well as ejection button 16 and button body 28 are created of a polymeric material. The polymeric material selected can have a low coefficient of friction such as polyoxymethylene (POM). A POM material or a similar material having a low coefficient of friction is selected at least for engagement post 36 to maintain the shape of engagement post 36 and to minimize frictional resistance between engagement post 36 and sled 34 as engagement post 36 slides within elongated slot 64, and as actuator arm 32 and therefore engagement post 36 rotate with respect to sled 34. According to other aspects, in lieu of a separate part, sled post 42 can be an integral extension of the material of actuator arm 32 and made such as by an injection molding or similar process during manufacture of actuator arm 32.

Referring to FIG. 6 and again to FIG. 5, to install sled 34 in sliding contact with the first and second guide rails 38, 40, the first and second chamfered ends 98, 100 of the first and second legs 80, 82 are initially oriented in parallel with the planar surfaces 78, 79 of the first and second guide rails 38, 40. This orients the first and second legs 80, 82 at an angle alpha (.alpha.) with respect to the planar surfaces 78, 79 of the first and second guide rails 38, 40. At this time, the first leg 80 is elastically outwardly displaced in an outward displacement direction "E", while the second leg 82 is elastically outwardly displaced in an outward displacement direction "F" oppositely directed with respect to outward displacement direction "E". Outward displacement of the first and second legs 80, 82 allows the first and second contact legs 94, 96 to be positioned into the wall notches 74 of first and second divider walls 72, 73. The biasing force created by leg outward displacement thereafter returns the first and second legs 80, 82 to the nominal leg positions by inward displacement opposite to the outward displacement directions "E", "F". The sled 34 is then rotated until the first and second legs 80, 82 contact and engage with the first and second guide rails 38, 40, and the first and second flanges 86, 88 of the cross member 84 are received in a cavity 102 defined between the first and second support walls 68, 70. The first flange 86 will contact the free ends of the insulator members 66 at a maximum sliding position of sled 34, defining the ejection position of sled 34. At an opposite sled displacement position, the first and second contact legs 94, 96 will contact inner edges of the wall notches 74 defining a test position of sled 34 where testing of the test strip 18 will be conducted.

Figure 6:
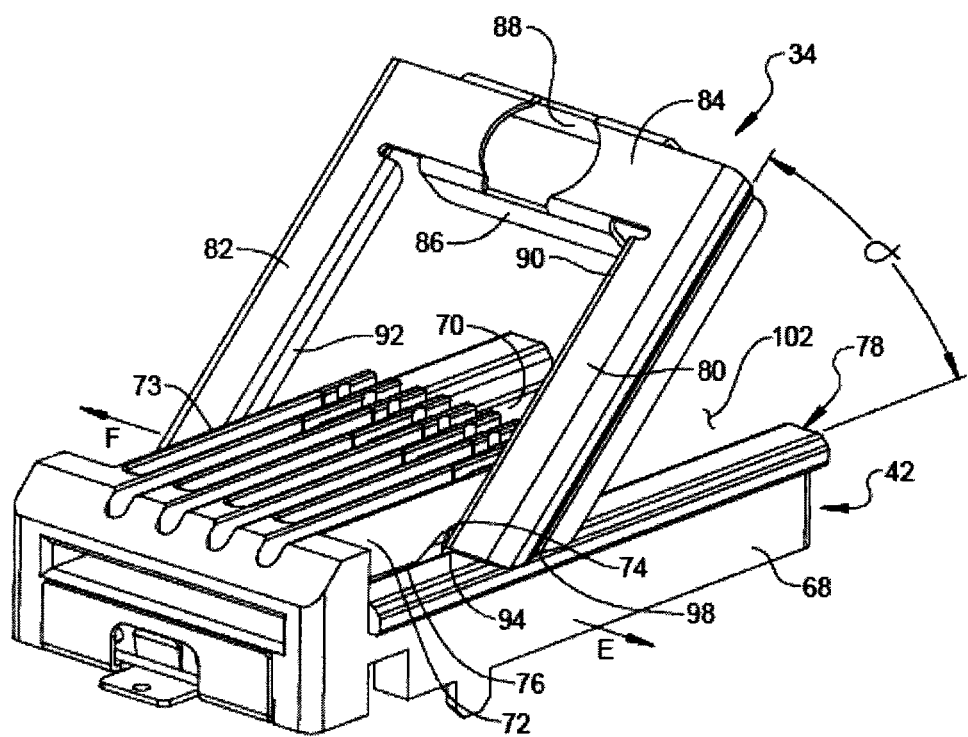
FIG. 6 shows a front perspective view of the sled and strip connector of FIG. 5 following initial angular installation of the sled.
Figure 7:
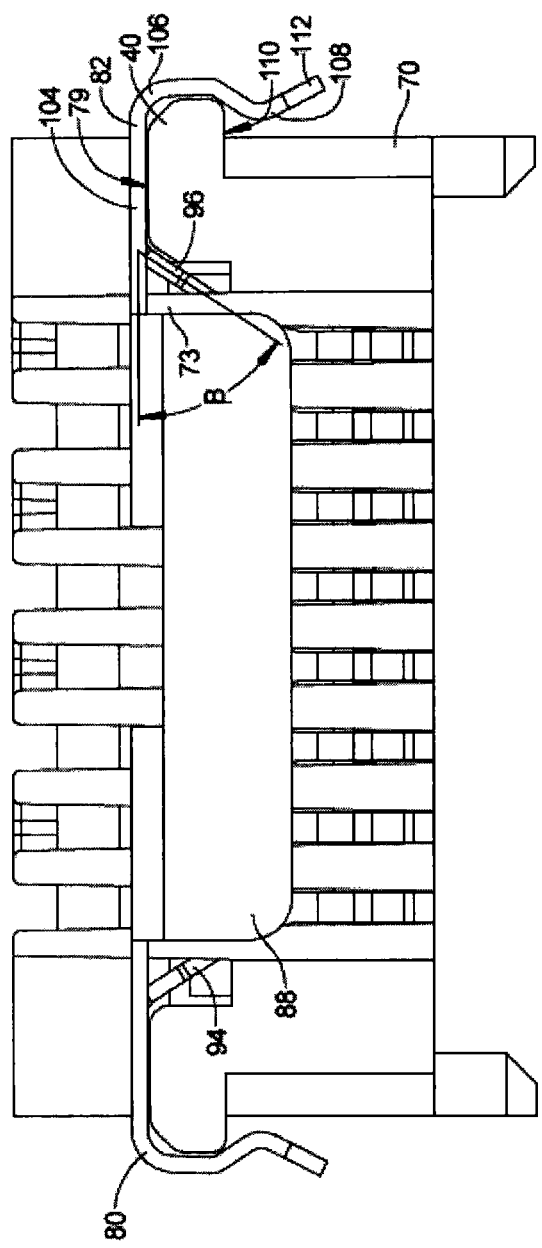
FIG. 7 shows and end elevational view of the assembled sled and strip connector.

Referring to FIG. 7 and again to FIGS. 5-6, the first leg 80 is a mirror image of second leg 82; therefore, the following discussion of the features of second leg 82 also applies equally to first leg 80. Second leg 82 includes a planar portion 104 which is oriented parallel and in sliding contact with the planar surface 79 of second guide rail 40. The planar portion 104 transitions into a convex portion 106 which contacts the outer face of second guide rail 40 thereby acting to prevent side-to-side motion of sled 34. A concave portion 108 is integrally connected to convex portion 106, and allows the second leg 82 to capture a bottom side 110 of second guide rail 40, thereby preventing sled 34 from lifting away from second guide rail 40 (in an upward direction as viewed in FIG. 7) during sliding motion of sled 34. A free end 112 of second leg 82 is angularly oriented away from second support wall 70 and provides a grip or contact portion to allow manual release of second leg 82 from second guide rail 40. The substantially U-shape defined by planar portion 104, convex portion 106 and concave portion 108 allows for sliding motion of sled 34, while preventing vertical release and/or side-to-side displacement of sled 34 with respect to the guide rails. The second contact leg 96 is angularly oriented with respect to planar portion 104, thereby defining an angle beta (.beta.). Angle .beta. can range from approximately 20 to approximately 70 degrees, which allows second contact leg 96 to be captured in the wall notch 74 of second divider wall 73. The first and second contact legs 94, 96 therefore act to further stabilize sled 34 against vertical release and/or against side-to-side displacement. The primary purpose of first and second contact legs, however, is to provide for direct contact between sled 34 and test strip 18. A length of the first and second contact legs 94, 96 is therefore predetermined such that free ends of the first and second contact legs 94, 96 are also positioned in the test strip receiving passage 20, thereby providing for direct contact between sled 34 and test strip 18 when test strip 18 is positioned in test strip receiving passage 20.

Figure 8:
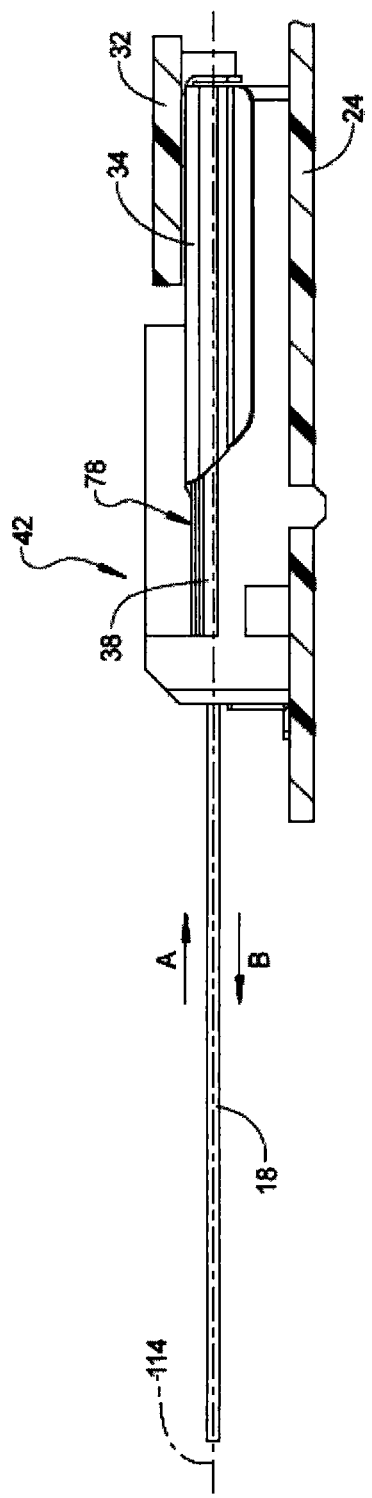
FIG. 8 shows a cross sectional side elevational view taken at section 8 of FIG. 3.

Referring to FIG. 8 and again to FIGS. 1-7, sled 34 is shown in the test strip 18 loaded or analysis test position such that a plane 114 extending through test strip 18 is oriented parallel to each of the planar surfaces 78, 79 of the first and second guide rails 38, 40 (only first guide rail 38 and planar surface 78 are visible in this view) and printed circuit board 24. Actuator arm 32 rotates parallel with respect to plane 114, which therefore minimizes the potential for binding or racking of sled 34 as it receives or ejects test strip 18 in either the loading direction "A" or ejection direction "B".

Referring to FIG. 9 and again to FIG. 3 the contact leg spacing "S" of first and second contact legs 94, 96 is selected to position first and second contact legs 94, 96 within test strip receiving channel 20 while providing as wide as possible contact leg spacing "S" at the maximum width of test strip 18. Contact between first and second contact legs 94, 96 with test strip 18 occurs at an end face 116 of test strip 18, which when received in test strip receiving channel 20 is oriented perpendicular to the first and second guide rails 38, 40. This also helps mitigate rotation or racking of sled 34 and/or test strip 18. Multiple electrical contacts 118 are individually positioned between successive pairs of the insulator members 66 and extend into cavity 102 where they are contacted by test strip 18 when in the test strip test position.

Referring to FIG. 10 and again to FIG. 3, according to further aspects, a sled 120 is modified from sled 34 to first and second legs 122, 124. Each of the first and second legs 122, 124 includes two slide guides, which help to further maintain sliding alignment and prevent racking of sled 120. First leg 122 includes first and second slide guides 126, 128, which can be formed for example from material of first leg 122 by a punching or stamping operation during formation of first leg 122. Second leg 124 similarly includes third and fourth slide guides 130, 132. First and second contact legs 94', 96' are provided with sled 120 and are similarly located and function the same as previously described in reference to first and second contact legs 94, 96. A cross member 134 joins first and second legs 122, 124, but is modified in design compared to cross member 84 of sled 34. Cross member 134 has first and second flanges 136, 138 which are oppositely directed compared to first and second flanges 86, 88. A sled elongated slot 140 functions the same as sled elongated slot 64 of sled 34.

Referring to FIG. 11 and again to FIGS. 5-6 and 9-10, sled 120 is shown after installation with strip connector 42, which is accomplished in the same manner as previously described with respect to sled 34. Installation in a sled installation direction "G" normal to a sliding direction of sled 34 allows sled 34 to be positioned directly over first and second guide rails 38, 40 and installed prior to installation of actuator arm 32 without interfering with any other component mounted on printed circuit board 24, or requiring the other component or components to be temporarily removed and/or installed at a later time than the installation of sled 34. This allows for automated machine installation of sled 34. During installation of sled 34 in the sled installation direction "G", the concave portion 108 of each of the individual legs 80, 82 deflects elastically outward with respect to the first or second guide rail 38, 40. When the concave portion 108 of each of the individual legs 80, 82 clears the first or second guide rail 38, 40, the legs 80, 82 elastically snap back to a non-deflected position. With the contact legs 94', 96' received in the rail wall notches 74, the sled 34 is thereby slidably coupled to the first and second divider walls 72, 73 and the first and second guide rails 38, 40, thereby limiting motion of sled 34 to sliding motion in either of the loading or ejection directions "A", "B".

Referring to FIGS. 1-11, for operation, the test strip ejector system 12 for receiving and ejecting test strip 18 from fluid analysis device 10 includes first and second guide rails 38, 40. Sled 34, 120 is slidably coupled with respect to one of the first or second guide rails 38, 40 for sliding motion in each of the loading direction "A" and the ejection direction "B". Actuator arm 32 is rotatably connected to the fluid analysis device 10. The sled 34, 120 is coupled to the actuator arm 32 such that rotation of the actuator arm 32 in a counter-clockwise loading rotational direction "H" as shown in FIG. 3 with respect to longitudinal axis 31 moves sled 34, 120 in the loading direction "A" and positions the sled 34, 120 in the test strip test position (shown in FIG. 3). Opposite rotation of the actuator arm 32 in a clockwise ejection rotational direction "J" operates to displace the sled 34, 120 in the ejection direction "B" away from the test strip test position and to position the first and second contact legs 94, 96 (or 94', 96') in direct contact with the test strip 18 to eject the test strip 18 from the analysis device 10.

As noted herein, test strip ejectors and systems of the present disclosure can be used in meters by individual users having personal test meters. Test strip ejector systems of the present disclosure can also be incorporated in commercial devices such as hospital meters, for example rechargeable test meters recharged by installation in a base unit, and/or blood glucose meters such as ACCU-CHEK® Inform System glucose meters manufactured by Roche Diagnostics. The test strips used by such hospital and glucose test meters can be configured differently from the test strips identified herein to conform to the requirements of the test and/or test meter, however the test strip ejector systems of the present disclosure will be similarly configured and function in a similar manner.

In addition, test strip ejectors and systems of the present disclosure can also be incorporated in individual or commercial devices such as blood coagulant test meters, for example blood clotting time test meters such as the COAGUCHEK® XS System coagulant test meters manufactured by Roche Diagnostics. The test strips used by such blood coagulant test meters can be configured differently from the test strips identified herein to conform to the requirements of the test and/or test meter, however the test strip ejector systems of the present disclosure will be similarly configured and function in a similar manner.

Test strip ejectors of the present disclosure offer several advantages. Sled 34, 120 of the present disclosure provides a sliding motion member that is retained by its deflectable legs externally to a parallel set of guide rails 38, 40. This provides a clear space or cavity 102 between the guide rails for sliding motion of the sled 34, 120 in direct contact with the test strip 18. The first and second contact legs 94, 96 (94', 96') of sled 34, 120 extend into rail wall notches 74 and channels 76 of the strip connector 42 so continuous contact with test strip 18 is maintained when test strip 18 is positioned in the test strip receiving port 20 and cavity 102 during sliding motion, at least in the ejection direction "B". According to other aspects, continuous contact between first and second contact legs 94, 96 (94', 96') of sled 34, 120 with test strip 18 can be maintained during all times when test strip 18 is positioned in cavity 102. The use of elastically flexible legs 80, 82 connected by the cross member 84 minimizes racking motion of sled 34, 120. The engagement post 36 of the actuator arm 32 which is received in the elongated slot 64, 140 of sled 34, 120 converts a rotational motion of actuator arm 32 into the sliding motion of sled 34, 120, minimizing the space required for the ejection mechanism assembly 26 on printed circuit board 24, while allowing the ejection mechanism assembly 26 to be mounted to a side of the guide rails in lieu of in axial relationship with the guide rails.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

The invention claimed is:

1. A test strip ejector system for receiving and ejecting a test strip of a fluid testing medical device, the system comprising:
   a strip connector defining a strip receiving passage configured to receive an end face of the test strip, the strip connector including
      a first guide rail,
      a second guide rail positioned opposite the first guide rail,
      wherein the strip receiving passage is located between the first guide rail and the second guide rail,
      a first divider wall positioned between the first guide rail and the second guide rail, wherein the first divider wall faces the first guide rail, wherein the first divider wall has a first edge with a first indentation that defines a first notch, and
      a second divider wall positioned between the first guide rail and the second guide rail, wherein the second divider wall faces the second guide rail, wherein the second divider wall has a second edge with a second indentation that defines a second notch;
   a sled configured to slide along the first guide rail and the second guide rail in a loading direction and an ejection direction, the sled including
      a first leg slidably engaged to the first guide rail, the first leg having a first contact leg extending into the first notch of the first divider wall to slidably couple the sled to the first divider wall, wherein the first contact leg extends into the strip receiving passage to contact the end face of the test strip during ejection from the strip receiving passage,
      a second leg slidably engaged to the second guide rail, the second leg having a second contact leg extending into the second notch of the second divider wall to slidably couple the sled to the second divider wall, wherein the second contact leg extends into the strip receiving passage to contact the end face of the test strip during ejection from the strip receiving passage, and
      a cross member connecting the first leg to the second leg;
   an ejection mechanism assembly coupled to the cross member of the sled, wherein the ejection mechanism assembly is configured to move the sled in the ejection direction to eject the test strip; and
   wherein the first contact leg and the second contact leg are aligned with one another to contact at the same time the end face of the test strip at two different locations to reduce any racking of the test strip in the strip receiving passage.

2. The test strip ejector system for receiving and ejecting a test strip of a fluid testing medical device of claim 1, wherein:
the second guide rail includes a planar surface upon which the second leg of the slide slides;
the second leg includes a planar portion configured to slide along the planar surface;
the planar portion extends parallel to the planar surface of the second guide rail; and
the second contact leg of the second leg being oriented at an angle relative to the planar portion that is in a range from 20 to 70 degrees.

3. The test strip ejector system for receiving and ejecting a test strip of a fluid testing medical device of claim 1, wherein the first leg and the second leg each include a chamfered end positioned opposite the cross member to facilitate insertion of the first contact leg into the first notch and the second contact leg into the second notch.

4. The test strip ejector system for receiving and ejecting a test strip of a fluid testing medical device of claim 3, the chamfered ends of the first leg and the second leg are free standing ends not joined by the cross member.

5. The test strip ejector system for receiving and ejecting a test strip of a fluid testing medical device of claim 4, wherein:
the first leg and the second leg each include a planar portion;
the first leg and the second leg are elastically flexible; and
the first leg and the second leg have an initial orientation before installation, wherein when in the initial orientation the planar portion of the first leg and the second leg are at an angle that is not parallel with respect to the first guide rail and the second guide rail, wherein when in the initial orientation the first leg and the second leg are deflected outwardly with respect to the first guide and the second guide rail to facilitate the sled is being installed in sliding contact with the first guide rail and the second guide rail.

6. The test strip ejector system for receiving and ejecting a test strip of a fluid testing medical device of claim 5, wherein:
the first leg and the second leg each include a planar portion; and
when in the initial orientation the planar portion of the first leg and the second leg are at an angle with respect to the first guide rail and the second guide rail.

7. The test strip ejector system for receiving and ejecting a test strip of a fluid testing medical device of claim 6, wherein:
the first guide rail and the second guide rail extend in the ejection direction; and
the first leg and the second leg have a subsequent orientation where the planar portion of the first leg and the second leg are rotated from the initial orientation to the subsequent orientation where the first leg and the second leg are parallel to the ejection direction allowing the first leg and the second leg to spring back to the initial spacing such that the first leg and the second leg are no longer deflected.

8. The test strip ejector system for receiving and ejecting a test strip of a fluid testing medical device of claim 7, wherein in the subsequent orientation the first leg and the second leg of the sled are slidably disposed on and snap fitted around the first guide rail and the second guide rail respectively to retain the sled in sliding continuous contact with the first guide rail and the second guide rail.

9. The test strip ejector system for receiving and ejecting a test strip of a fluid testing medical device of claim 1, wherein the first divider wall at the first notch includes a wall positioned to contact the first contact leg of the sled to position the sled at a test position for the test strip.

10. The test strip ejector system for receiving and ejecting a test strip of a fluid testing medical device of claim 1, wherein:
the strip connector includes multiple insulator members having ends facing the cross member of the sled, wherein the insulative members are made of insulative material; and
the cross member of the sled being positioned to contact the ends of the insulator members to limit travel of the sled moved in the ejection direction.

\* \* \* \* \*